United States Patent
Li et al.

(10) Patent No.: US 12,385,832 B2
(45) Date of Patent: Aug. 12, 2025

(54) TERAHERTZ WAVE DETECTION CHIP AND TERAHERTZ WAVE DETECTION SYSTEM

(71) Applicant: INDUSTRIAL TECHNOLOGY RESEARCH INSTITUTE, Hsinchu (TW)

(72) Inventors: Yu-Tai Li, Taichung (TW); Kao-Chi Lin, Kaohsiung (TW); Cho-Fan Hsieh, Luodong Township (TW); Teng-Chun Wu, Jinning Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 357 days.

(21) Appl. No.: 18/087,462

(22) Filed: Dec. 22, 2022

(65) Prior Publication Data
US 2024/0151642 A1    May 9, 2024

(30) Foreign Application Priority Data

Nov. 9, 2022  (TW) .................................. 111142843

(51) Int. Cl.
| | | |
|---|---|---|
| *G01N 29/22* | (2006.01) | |
| *G01N 1/28* | (2006.01) | |
| *G01N 21/3581* | (2014.01) | |
| *G01N 29/34* | (2006.01) | |
| *G01N 21/84* | (2006.01) | |

(52) U.S. Cl.
CPC ........... *G01N 21/3581* (2013.01); *G01N 1/28* (2013.01); *G01N 29/223* (2013.01); *G01N 29/34* (2013.01); *G01N 2021/8438* (2013.01)

(58) Field of Classification Search
CPC .. G01R 31/2623; G01R 31/261; G01R 21/06; G01R 19/30; G01R 19/00; G01R 15/144; G01R 15/12
See application file for complete search history.

(56) References Cited

U.S. PATENT DOCUMENTS

| | | | |
|---|---|---|---|
| 9,551,655 | B2 | 1/2017 | Mazumder et al. |
| 2018/0237850 | A1* | 8/2018 | Mandell ............. G01R 33/1276 |
| 2021/0210643 | A1 | 7/2021 | Shimatani et al. |
| 2021/0239611 | A1 | 8/2021 | Al-Naib |
| 2023/0204695 | A1* | 6/2023 | Deeg ..................... B01L 3/5085 |
| | | | 324/304 |

FOREIGN PATENT DOCUMENTS

| | | |
|---|---|---|
| CN | 108267417 A | 7/2018 |
| CN | 110105512 A | 8/2019 |
| CN | 111610155 A | 9/2020 |
| CN | 113466170 A | 10/2021 |
| TW | 202212819 A | 4/2022 |

OTHER PUBLICATIONS

TW Office Action dated Jul. 17, 2023 as received in Application No. 111142843.
Shen et al. "Recent Advances in the Development of Materials for Terahertz Metamaterial Sensing" Advanced Optic Materials Oct. 2021 DOI: 10.1002/adom.202101008.

* cited by examiner

*Primary Examiner* — Tung X Nguyen
(74) *Attorney, Agent, or Firm* — Maschoff Brennan

(57) ABSTRACT

A terahertz wave detection chip includes a substrate and at least one detection structure. The detection structure is disposed on a surface of the substrate. The detection structure includes a metamaterial layer and a hydrophilic layer, and the hydrophilic layer is disposed on the metamaterial layer.

20 Claims, 8 Drawing Sheets

US 12,385,832 B2

TERAHERTZ WAVE DETECTION CHIP AND TERAHERTZ WAVE DETECTION SYSTEM

CROSS-REFERENCE TO RELATED APPLICATIONS

This application claims priority under 35 U.S.C. § 119(a) on Patent Application No(s). 111142843 filed in Taiwan, R.O.C. on Nov. 9, 2022, the entire contents of which are hereby incorporated by reference.

TECHNICAL FIELD

This present disclosure relates to a terahertz wave detection chip and a terahertz wave detection system.

BACKGROUND

Amongst the existing technologies, the enzyme-linked immunosorbent assay (ELISA) or surface plasma resonance (SPR) technologies are mostly used for bio-detection. However, using these two technologies requires targeting the testing sample with a marker as well as amplifying the detected signal to obtain a valid detection value, which causes the increase in detection time. In addition, since using these two technologies requires consuming chemicals (such as dyeing agents) or ligand when preparing the testing sample, the cost of bio-detection also increases accordingly.

At present, the implementation of bio-detection by terahertz waves has been proposed, and the terahertz wave detection overcomes the disadvantages of ELISA and SPR. The terahertz wave detection can be used with metamaterials to amplify the strength of the terahertz wave signals so as to be suitable in various applications.

SUMMARY

According to one embodiment of the present disclosure, a terahertz wave detection chip includes a substrate and at least one detection structure. The detection structure is disposed on a surface of the substrate. The detection structure includes a metamaterial layer and a hydrophilic layer, and the hydrophilic layer is disposed on the metamaterial layer.

According to another embodiment of the present disclosure, a terahertz wave detection system includes a terahertz wave detection chip, a transmitter, a receiver and a processor. The terahertz wave detection chip includes a substrate and a detection structure. The detection structure is disposed on a surface of the substrate. The detection structure includes a metamaterial layer and a hydrophilic layer, the hydrophilic layer is disposed on the metamaterial layer, and the metamaterial layer includes a resonance pattern. The transmitter is configured to deliver a terahertz wave corresponding to the resonance pattern in the terahertz wave detection chip. The receiver is configured to receive a reflected wave corresponding to the terahertz wave from the terahertz wave detection chip. The processor is in signal-transmittable connection with the receiver. The processor obtains the reflected wave from the receiver and determines a detected object characteristic according to the reflected wave.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present disclosure. The following embodiments further illustrate various aspects of the present disclosure, but are not meant to limit the scope of the present disclosure.

Figure 1:
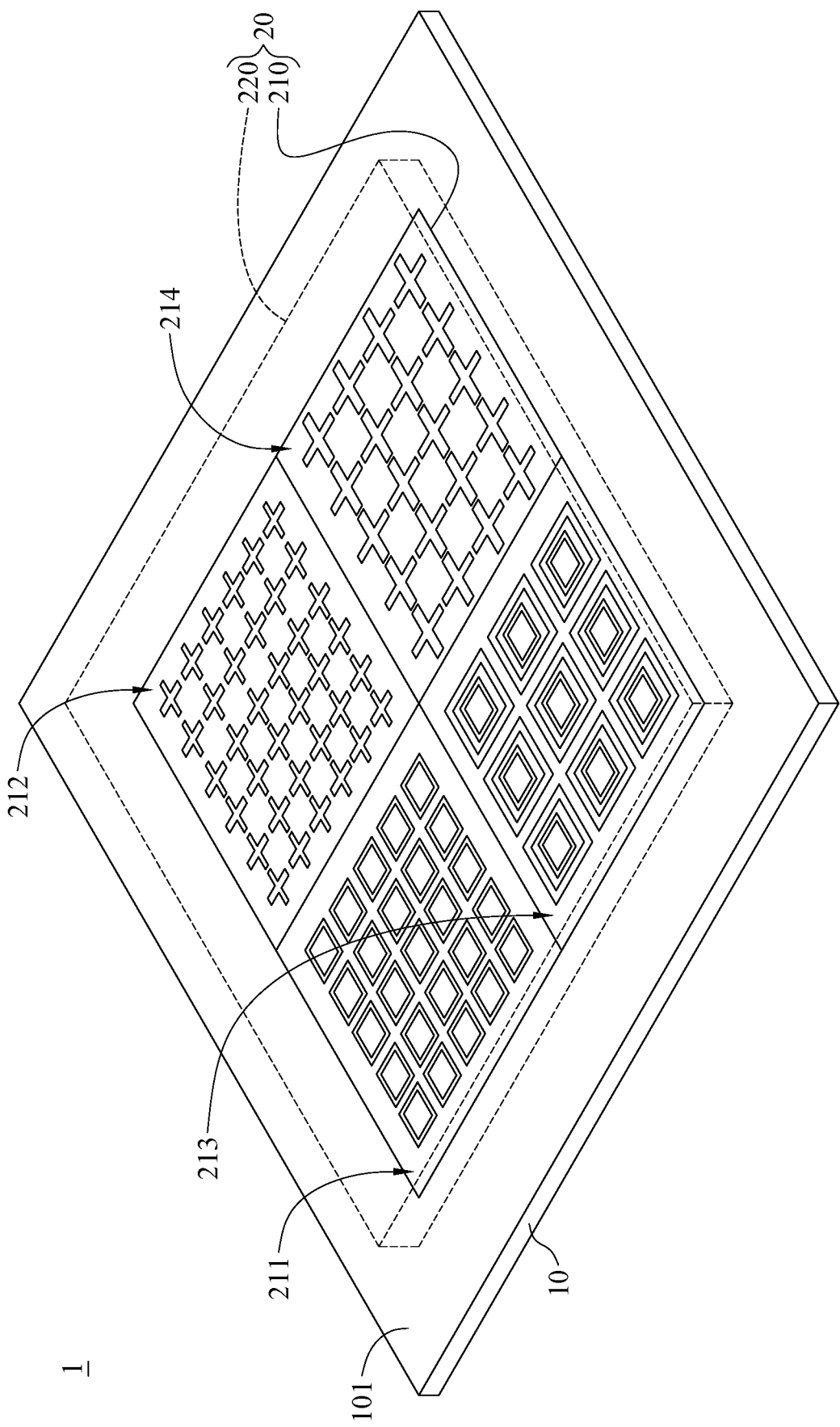
FIG. 1 is a schematic view of a terahertz wave detection chip according to one embodiment of the present disclosure.
Figure 2:
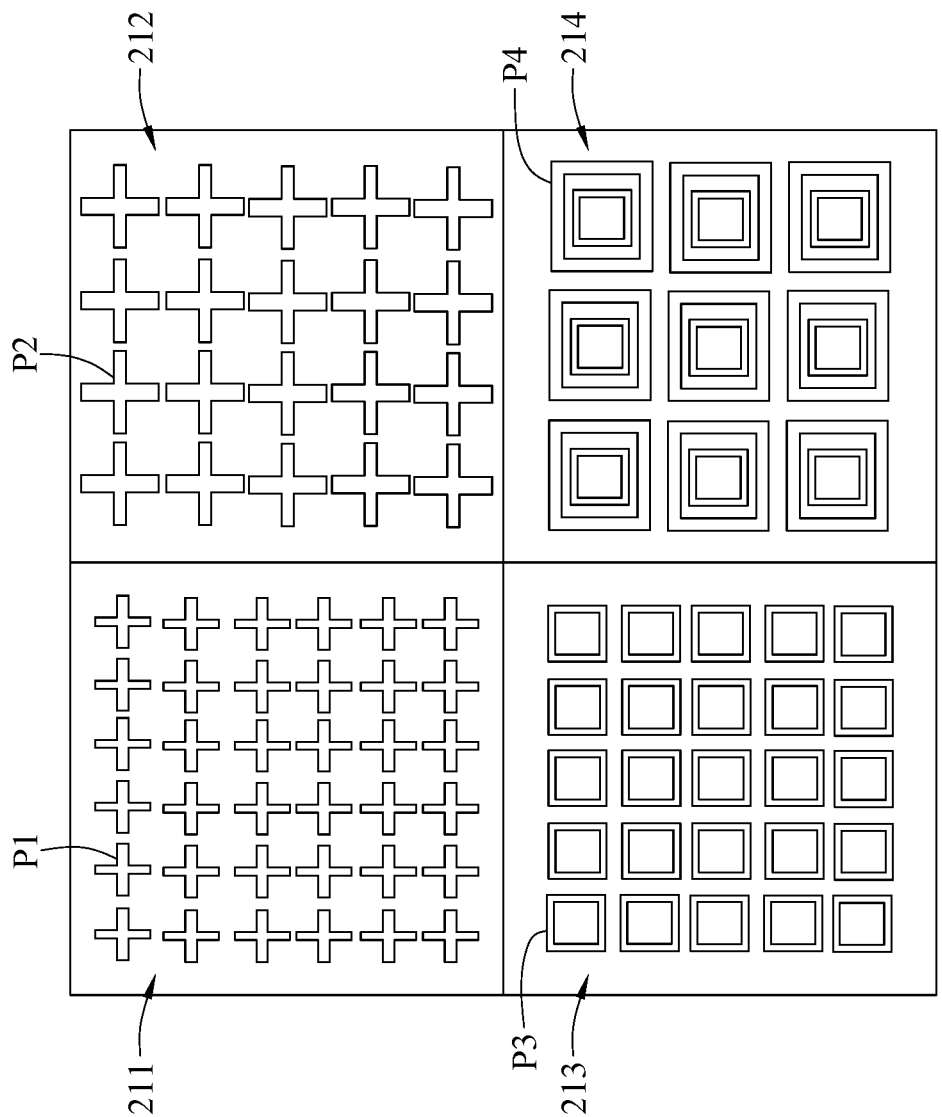
FIG. 2 is a schematic view of a metamaterial layer of the terahertz wave detection chip in FIG. 1.

Please refer to FIG. 1 and FIG. 2. FIG. 1 is a schematic view of a terahertz wave detection chip according to one embodiment of the present disclosure, and FIG. 2 is a schematic view of a metamaterial layer of the terahertz wave detection chip in FIG. 1. In this embodiment, a terahertz wave detection chip 1 may include a substrate 10 and a detection structure 20, and the detection structure 20 is disposed on a top surface 101 of the substrate 10.

The substrate 10 is, for example but not limited to, made of plastic or glass. In this embodiment, the substrate 10 may be made of polydimethylsiloxane (PDMS) or other materials allowing transmission of terahertz wave. The detection structure 20 may include a metamaterial layer 210 and a hydrophilic layer 220, and the hydrophilic layer 220 is disposed on the metamaterial layer 210.

The metamaterial layer 210 has a plurality of regions, and each of the regions has a plurality of resonance elements. A resonance pattern is formed by the resonance elements in any one of the regions. The resonance patterns in respective regions generate resonance for different incident waves (such as terahertz waves) corresponding to different resonance frequencies. By adopting the terahertz waves and the metamaterial layer 210, the detected signal may be efficiently amplified to provide accurate and valid detection data. As shown in FIG. 2, the metamaterial layer 210 may include a first region 211, s second region 212, a third region 213 and a fourth region 214, and each of the first region 211 through the fourth region 214 may be in a shape of square. The first region 211 through the fourth region 214 may have different resonance elements P1 to P4, respectively, and the resonance elements in respective region are periodically arranged to form a resonance pattern, but the present disclosure is not limited thereto. The resonance elements in respective region may be arranged irregularly. In other words, each of the first region 211 through the fourth region 214 may have multiple microstructures, the microstructures in the same region are repeatedly and regularly arranged, and the microstructures of each region may form as the resonance pattern in that region. The metamaterial layer 210 may be formed on the substrate 10 by at least one of metal micro-printing, cathodic etching, metal evaporation and ion-beam etching, but the present disclosure is not limited the formation of the metamaterial layer 210. The microstructure as each of the resonance elements P1 to P4 may be cross-shaped, square, C-shaped, circular, oval or bow-shaped. The present disclosure is not limited to the shape of the microstructure.

The resonance elements P1 to P4 may have different shapes to thereby correspond to different resonance frequencies. Further, the resonance frequencies are preferably equally spaced, and the highest resonance frequency among the resonance frequencies may be the highest detectable frequency of a receiver for receiving a reflected wave. For example, when the highest detectable frequency is 1 terahertz (THz), the resonance frequencies of the resonance elements P1 to P4 may be 0.4 THz, 0.6 THz, 0.8 THz and 1 THz, respectively. In addition, the resonance frequencies of the resonance elements P1 to P4 may also be equally spaced within the range of 0.1 THz to 3 THz. The present disclosure is not limit to the range of the resonance frequency of the resonance elements P1 to P4.

The object to be detected may be provided for the terahertz wave detection chip 1, and the terahertz wave detection chip 1 is used to measure the physical properties (for example, difference in refraction indices or dielectric coefficients) of the object. Four pieces of data may be obtained at the same time because the first region 211 through the fourth regions 214 with different resonance elements P1 to P4 are disposed, which is helpful to reduce cost and time required for performing detection. Further, by setting the resonance frequencies to be equally spaced within a range with the highest detectable frequency being the upper limit of said range, the overall physical properties of the object corresponding to said range may be obtained more efficiently. Accordingly, a user may determine the characteristics (for example, refraction indices and/or dielectric coefficients) of the detected object based on the four pieces of data, and determine what the object is based on a pre-established table recording the correspondence between refraction indices and/or dielectric coefficients and item names.

Figure 3:
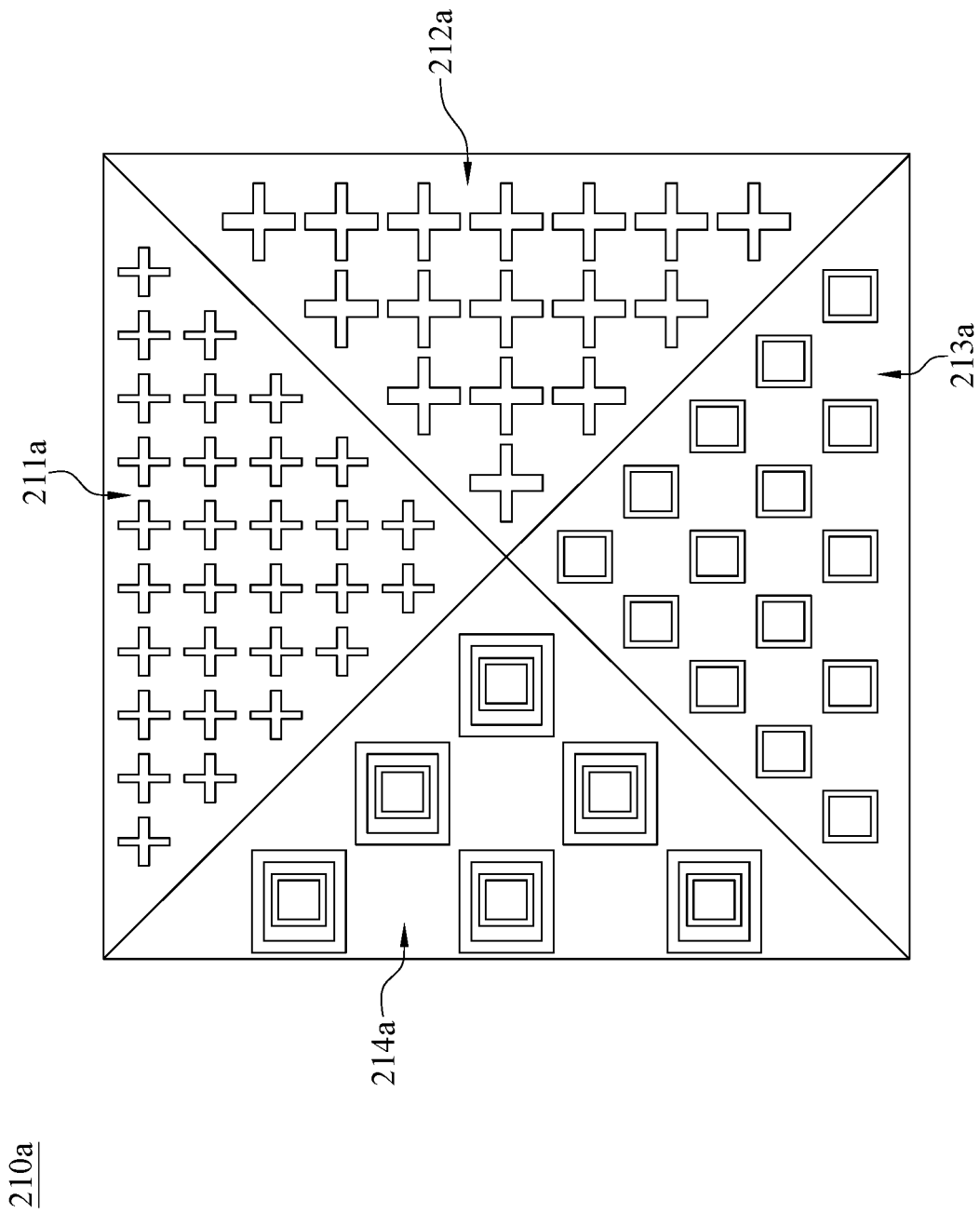
FIG. 3 is a schematic view of a metamaterial layer according to another embodiment of the present disclosure.

It is noted that the resonance patterns of the metamaterial layer 210 are not limited to that shown in FIG. 2. The resonance patterns may have various appearances depending on the required resonance frequency/amplitude. FIG. 3 is a schematic view of a metamaterial layer according to another embodiment of the present disclosure. The metamaterial layer 210a according to this embodiment may include a first region 211a, a second 212a, a third 213a and a fourth region 214a, and each of the first region 211a through the fourth region 214a may be in a shape of isosceles triangle. The resonance frequencies of the resonance elements P1 to P4 of the first region 211a through the fourth region 214a may also be equally spaced, and the highest resonance frequency among the four resonance frequencies may be the highest detectable frequency of a receiver for receiving a reflected wave.

In some other embodiments, the metamaterial layer may have eight regions with different resonance patterns or nine regions with different resonance patterns, and the regions may be in the shape of rectangle, triangle, etc. The present disclosure does not limit the amount, shape and frequency of regions of the metamaterial layer.

Figure 4:
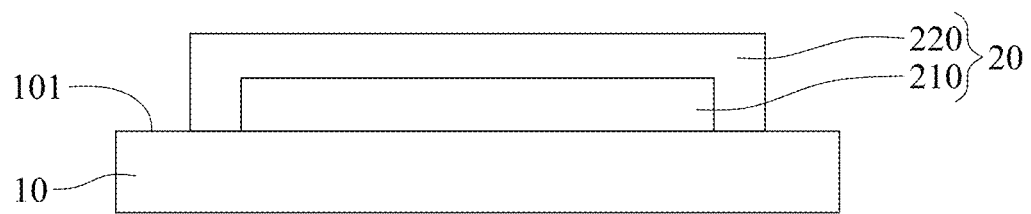
FIG. 4 is a cross-sectional view of a detection structure of the terahertz wave detection chip in FIG. 1.

The relationship between the hydrophilic layer 220 and the metamaterial layer 210 is further described hereafter. FIG. 4 is a cross-sectional view of a detection structure of the terahertz wave detection chip in FIG. 1. The hydrophilic layer 220 of the detection structure 20 is disposed on the top surface 101 of the substrate 10 and encapsulates the metamaterial layer 210. Specifically, the hydrophilic layer 220 may include photocured material, such as UV curing resin. After the formation of the metamaterial layer 210, the UV curable resin in gel form may be spread over the top surface of the substrate 10 and the metamaterial layer 210, and may be stood for a while to flow to cover the top surface and the later surface of the metamaterial layer 210. Then, the resin is cured by UV light. The hydrophilic layer 220 may be transparent or opaque, and the hydrophilic layer 220 allows the transmission of terahertz waves.

Figure 5:
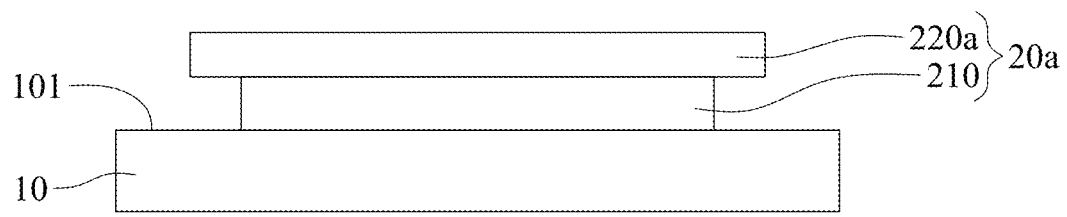
FIG. 5 is a cross-sectional view of a detection structure according to another embodiment of the present disclosure.

The relationship between the hydrophilic layer and the metamaterial layer is not limited to the configuration in FIG. 4. FIG. 5 is a cross-sectional view of a detection structure according to another embodiment of the present disclosure. A detection structure 20a according to an embodiment of the present disclosure may include a metamaterial layer 210 and a hydrophilic layer 220a. The metamaterial layer 210 is disposed between the substrate 10 and the hydrophilic layer 220a, and the hydrophilic layer 220a is adhered to the metamaterial layer 210. Specifically, the bottom surface of the metamaterial layer 210 may physically contact the top surface 101 of the substrate 10. The top surface of the metamaterial layer 210 may physically contact the hydrophilic layer 220a, and the hydrophilic layer 220a may be spatially separated from the substrate 10. The hydrophilic layer 220a may include a plastic film with hydrophilic coating. For example, the surface of the hydrophilic layer 220a may be treated by air plasma or coated with a PET (polyethylene terephthalate) film containing photocatalysts. The hydrophilic layer 220a may be transparent or opaque, and the hydrophilic layer 220a allows the transmission of terahertz waves. Also, the hydrophilic layer 220a may also the function of transferring the metamaterial layer 210, since the adhesion between the hydrophilic layer 220a and the metamaterial layer 210 may be stronger than the adhesion between the hydrophilic layer 220a and the substrate 10, such that the metamaterial layer 210 can be removed from the substrate 10 by tearing off the hydrophilic layer 220a, and the hydrophilic layer 220a and the metamaterial layer 210 can be jointly transferred to another substrate.

Figure 6:
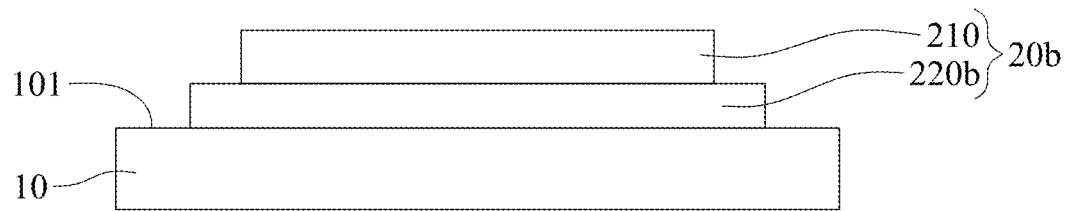
FIG. 6 is a cross-sectional view of a detection structure according to still another embodiment of the present disclosure.

FIG. 6 is a cross-sectional view of a detection structure according to still another embodiment of the present disclosure. A detection structure 20b according to an embodiment of the present disclosure may include a metamaterial layer 210 and a hydrophilic layer 220b. The hydrophilic layer 220b is disposed between the substrate 10 and the metamaterial layer 210, and the hydrophilic layer 220b is adhered to the top surface 101 of the substrate 10. In detail, the bottom surface of the hydrophilic layer 220b may physically contact the top surface 101 of the substrate 10, the top surface of the hydrophilic layer 220b may physically contact the metamaterial layer 210, and the metamaterial layer 210 may be spatially separated from the substrate 10. The hydrophilic layer 220b may include a plastic film with hydrophilic coating or a glass cloth tape. For example, the hydrophilic layer 220b may be treated by air plasma or coated with a PET film containing photocatalysts. The hydrophilic layer 220b may be transparent or opaque, and the hydrophilic layer 220b allows the transmission of terahertz waves.

Figure 7:
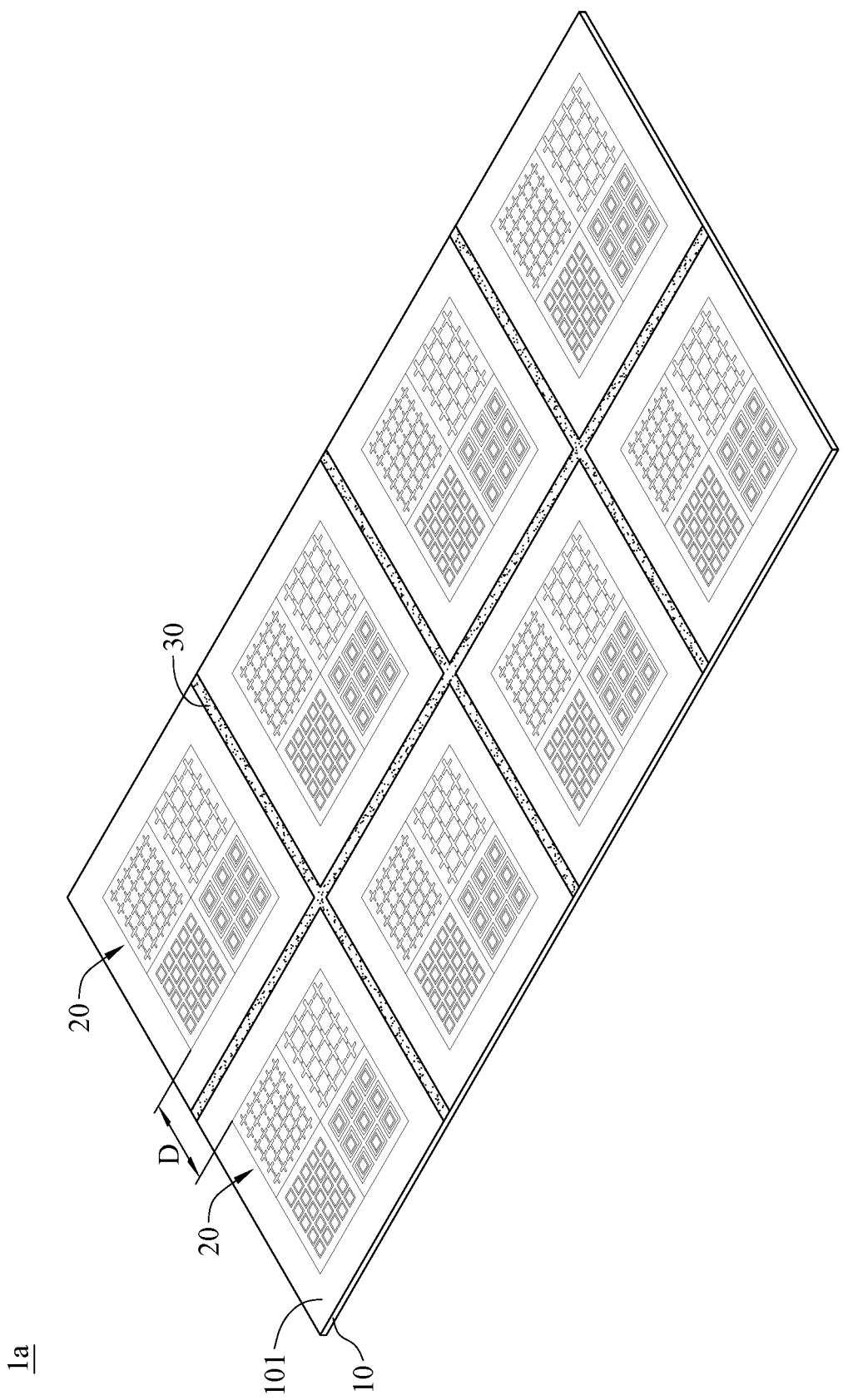
FIG. 7 is a schematic view of a terahertz wave detection chip according to another embodiment of the present disclosure.

The detection chip may include multiple detection structures according to one embodiment of the present disclosure. FIG. 7 is a schematic view of a terahertz wave detection chip according to another embodiment of the present disclosure. A terahertz wave detection chip 1a according to an embodiment of the present disclosure may include a substrate 10, a plurality of detection structures 20 and a hydrophobic coating 30. The specific configuration of each detection structure 20 can be referred to FIG. 1 through FIG. 4, and the description thereof will be omitted hereafter. The detection structures 20 may be periodically arranged on the top surface 101 of the substrate 10. The hydrophobic coating 30 is disposed on the top surface 101 of the substrate 10 and located between adjacent detection structures 20. The hydrophobic coating 30 may be made of polytetrafluoroethylene (PTFE), fluorinated polyethylene, fluorocarbon wax or other synthetic fluoropolymers that are prone to hydrophobic properties.

Figure 8:
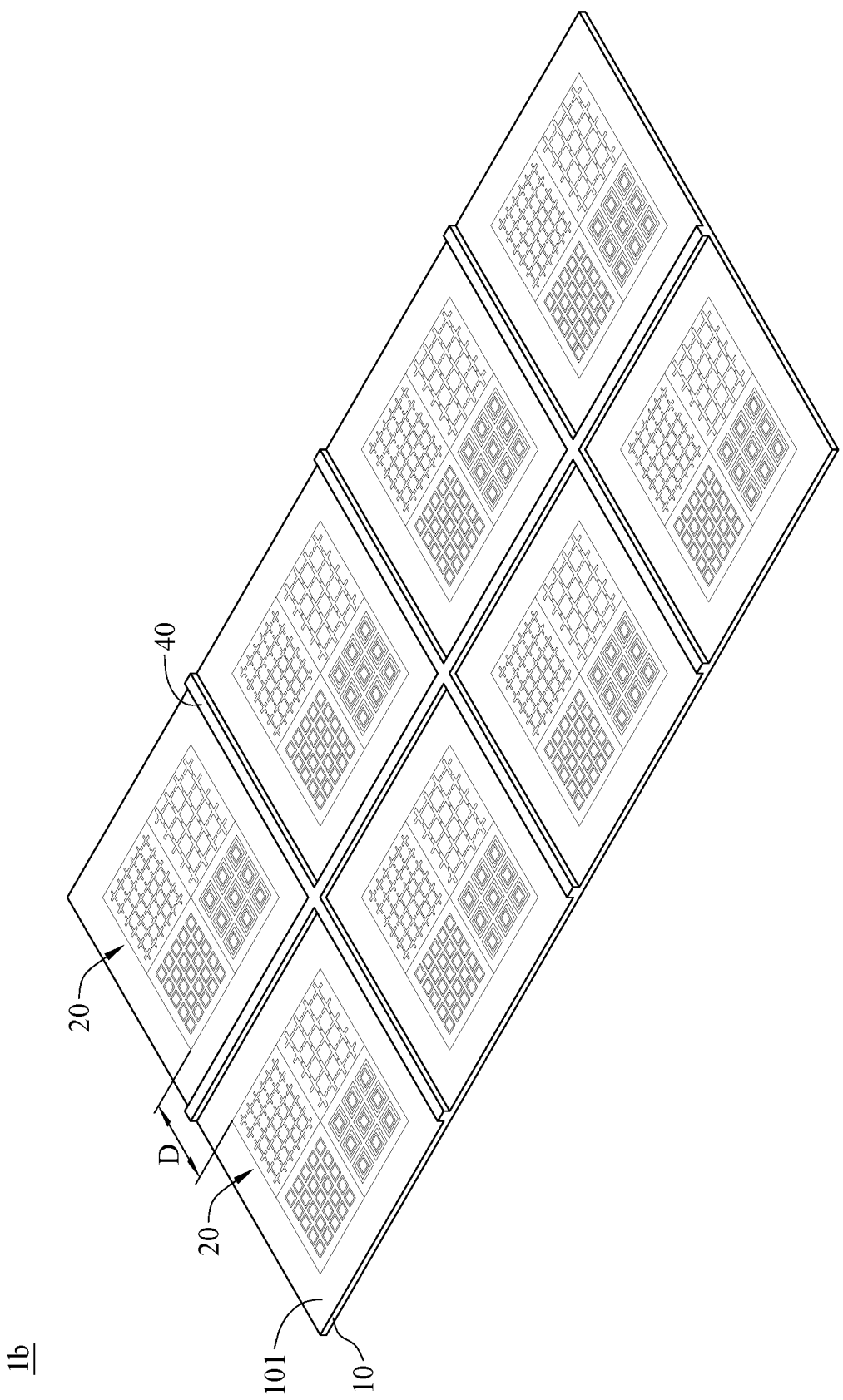
FIG. 8 is a schematic view of a terahertz wave detection chip according to still another embodiment of the present disclosure.

FIG. 8 is a schematic view of a terahertz wave detection chip according to still another embodiment of the present disclosure. A terahertz wave detection chip 1b according to an embodiment of the present disclosure may include a substrate 10, a plurality of detection structures 20 and a partition 40. The specific configuration of each detection structure 20 can be referred to FIG. 1 through FIG. 4, and the description thereof will be omitted hereafter. The detection structures 20 may be periodically arranged on the top surface 101 of the substrate 10. The partition 40 is disposed on the top surface 101 of the substrate 10 and located between adjacent detection structures 20. The partition 40 may be made of the same material as the substrate 10, such that the partition 40 and the substrate 10 are jointly formed in one piece.

When a microdroplet containing objects such as pharmaceutical ingredients or proteins is provided to one of the detection structures, the hydrophilic layer 220 in FIG. 4, the hydrophilic layer 220a in FIG. 5 and the hydrophilic layer 220b in FIG. 6 are helpful to enlarge the solid-liquid interface of the microdroplet, thus allowing the objects to be evenly distributed over the effective area (for example, the first region 211, the second region 212, the third region 213 and the fourth region 214 in FIG. 2) of the metamaterial layer 210. The spread of the microdroplet on the hydrophilic detection structure allows the implementation of terahertz wave detection by providing the microdroplet with low concentration objects. In addition, the hydrophilic layer is also helpful to make the liquid in the microdroplet evaporate quickly, thus preventing the disturbance of terahertz wave detection due to residual liquid on the detection structure. Also, the hydrophilic layer 220 in FIG. 4 and the hydrophilic layer 220a in FIG. 5 can protect the metal metamaterial layer 210 from being damaged or peeled off.

The terahertz wave detection chip 1a in FIG. 7 and the terahertz wave detection chip 1b in FIG. 8 provide a matrix consisting of multiple detection structures 20, which enables rapid detection of large amount of samples to be detected. It is allowed to detect multiple samples with different concentrations of objects to be detected or containing different types of objects to be detected at the same time. For example, a microdroplet with low protein concentration and a microdroplet with high protein concentration may be provided to two of the detection structures 20, respectively; or, a microdroplet containing certain herbal extract and a microdroplet containing another herbal extract may be provided to two of the detection structures 20, respectively. The hydrophobic coating 30 in FIG. 7 and the partition 40 in FIG. 8 can prevent the microdroplet on one of the detection structures 20 from overflowing to the other detection structures 20 in the vicinity. Furthermore, for the purpose of wide application of the detection chip disclosed herein, each detection structure 20 in FIG. 7 and FIG. 8 may have an area equal to or less than 100.0 mm$^2$, and a distance between any two of the detection structures 20 adjacent to each other may be greater than 2.0 mm.

Figure 9:
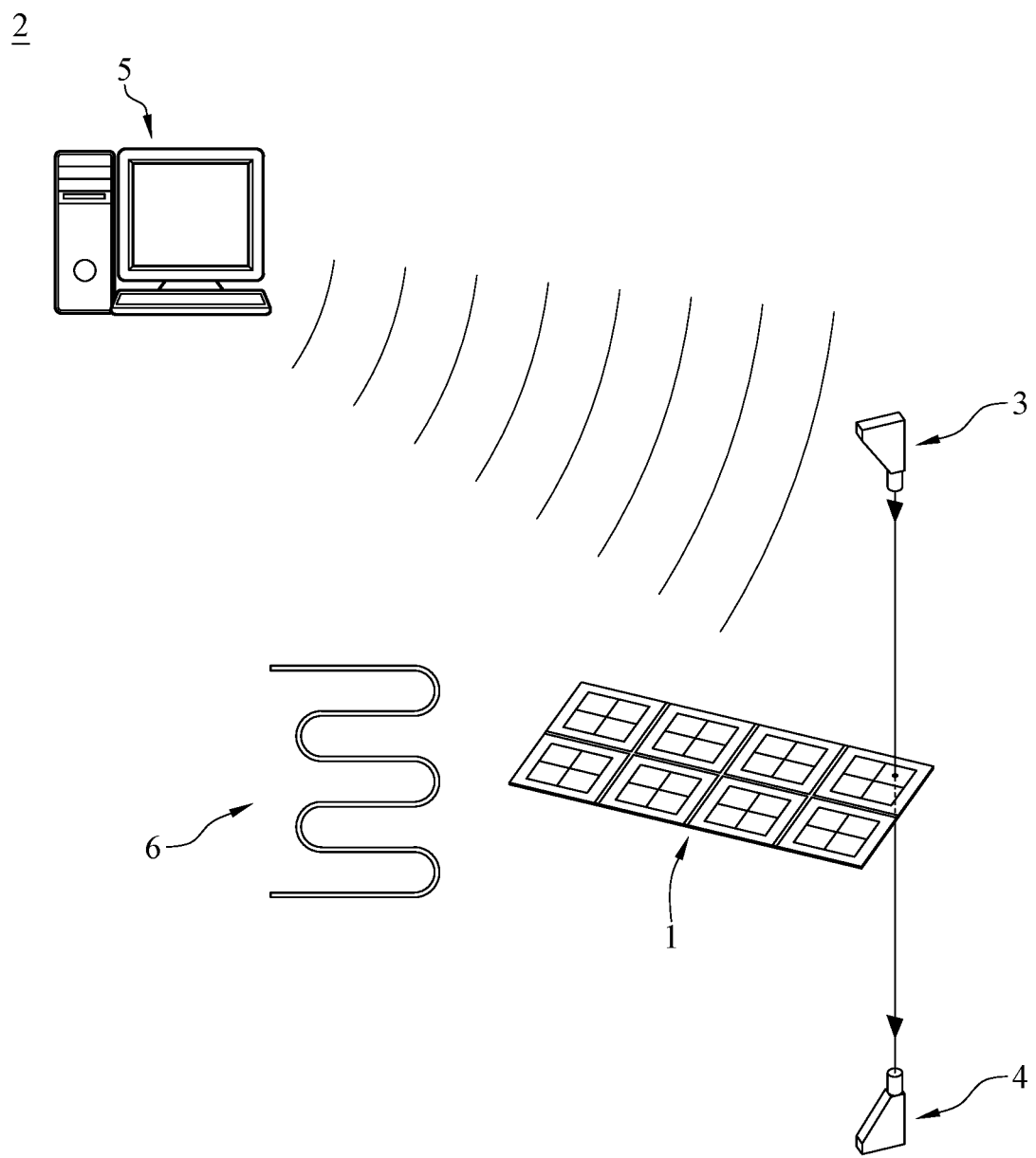
FIG. 9 and FIG. 10 are schematic views of a terahertz wave detection system according to one embodiment of the present disclosure.
Figure 10:
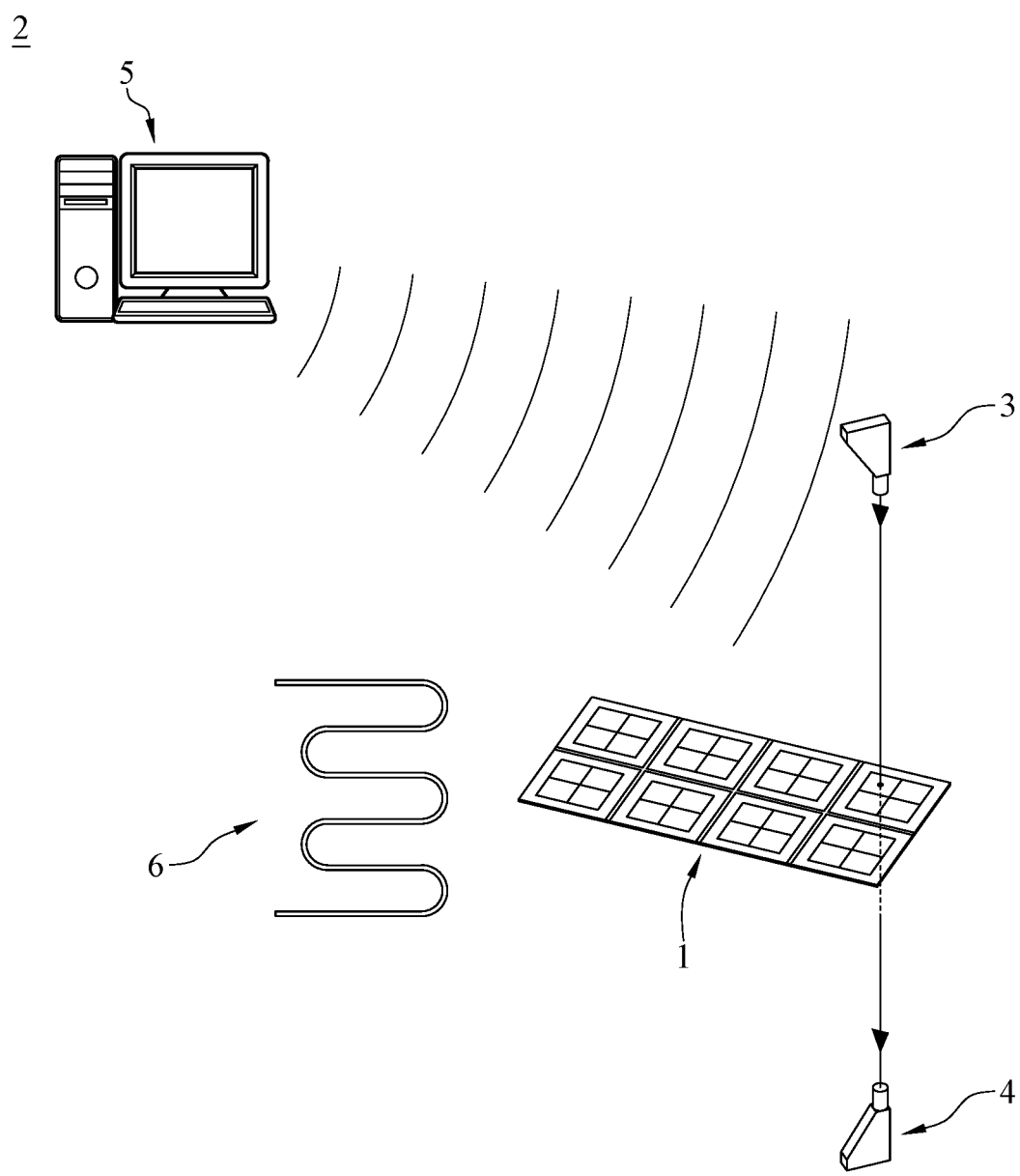

FIG. 9 and FIG. 10 are schematic views of a terahertz wave detection system according to one embodiment of the present disclosure. In this embodiment, a terahertz wave detection system 2 may include the terahertz wave detection chip according to any embodiment of the present disclosure, a transmitter 3, a receiver 4 and a processor 5. The terahertz wave detection chip may be the terahertz wave detection chip 1, the terahertz wave detection chip 1a or the terahertz wave detection chip 1b mentioned above. FIG. 9 and FIG. 10 exemplarily depict the terahertz wave detection chip 1 included in the terahertz wave detection system 2.

The processor 5 is in signal-transmittable connection with the transmitter 3 and the receiver 4. The processor 5 controls the transmitter 3 to emit terahertz waves, and receives a reflected wave reflected from the terahertz wave detection chip 1 by the receiver 4. The frequency of terahertz waves emitted by the transmitter 3 may range, for example, from 0.1 THz to 10 THz, but the present disclosure does not limit the frequency of terahertz waves emitted by the transmitter 3, however.

The transmitter 3 is configured to emit a terahertz wave to the terahertz wave detection chip 1, and the emitted terahertz wave corresponds to the resonance pattern. Referring to FIG. 1, FIG. 9 and FIG. 10, the processor 5 can control the transmitter 3 to emit the terahertz wave corresponding to the resonance pattern in the first region 211 of the metamaterial layer 210 of one of the detection structures 20, and control the receiver 4 to receive the corresponding reflected wave.

The processor 5 can control the transmitter 3 and the receiver 4 to move to a position corresponding to the second region 212 of the metamaterial layer 210 of the same detection structure 20. The processor 5 can control the transmitter 3 to emit the terahertz wave corresponding to the resonance pattern in the second region 212, and control the receiver 4 to receive the corresponding reflected wave. Therefore, the processor 5 may obtain the physical properties of the reflected wave corresponding to every region on the metamaterial layer 210 of each detection structure 20 of the terahertz wave detection chip 1. Since the resonance patterns of respective regions on the metamaterial layer 210 corresponds to different resonance frequencies, the processor 5 may obtain the differences of the physical properties between each terahertz wave and each reflected wave under different resonance frequency. The differences between the physical properties may include the difference in frequency or amplitude.

In order to make the microdroplets provided to the terahertz wave detection chip 1 evaporate quickly, the terahertz wave detection system 2 may further include a drying tool 6 disposed corresponding to the terahertz wave detection chip 1. The drying tool 6 may include a heater or a purge gas supplier. For example, as shown in FIG. 9 and FIG. 10, the drying tool 6 may include a tubular electric heater around the terahertz wave detection chip 1. In another embodiment, the drying tool may include a heating plate for carrying the terahertz wave detection chip. In still another embodiment, the drying tool may include a purge gun (purge gas supplier) that can blow nitrogen gas to remove liquid.

According to the present disclosure, the detection structure includes a metamaterial layer and a hydrophilic layer.

When a microdroplet containing objects such as pharmaceutical ingredients or proteins are provided to the detection structure, the hydrophilic layer is helpful to enlarge the solid-liquid interface of the microdroplet, thus allowing the objects to be evenly distributed over each region of the metamaterial layer. The spread of the microdroplet on the hydrophilic detection structure allows the implementation of terahertz wave detection by providing the microdroplet with low concentration objects. In addition, the hydrophilic layer is helpful to make the liquid in the microdroplet evaporate quickly, thus preventing the disturbance of terahertz wave detection due to residual liquid on the detection structure. Also, the hydrophilic layer protects the metal metamaterial layer from being damaged or rustiness.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A terahertz wave detection chip, comprising:
   a substrate; and
   at least one detection structure disposed on a surface of the substrate, wherein the at least one detection structure comprises a metamaterial layer and a hydrophilic layer, and the hydrophilic layer is disposed on the metamaterial layer;
   wherein the hydrophilic layer facilitates spreading of a microdroplet containing a low concentration object over the metamaterial layer, thereby enabling detection of changes in dielectric properties via frequency shifts in reflected terahertz waves.

2. The terahertz wave detection chip according to claim 1, wherein the metamaterial layer is formed on the substrate by at least one of metal micro-printing, cathodic etching, metal evaporation and ion-beam etching.

3. The terahertz wave detection chip according to claim 1, wherein the hydrophilic layer is disposed on the surface of the substrate and encapsulates the metamaterial layer.

4. The terahertz wave detection chip according to claim 3, wherein the hydrophilic layer comprises photocured material.

5. The terahertz wave detection chip according to claim 1, wherein the metamaterial layer is disposed between the substrate and the hydrophilic layer, and the hydrophilic layer is adhered to the metamaterial layer.

6. The terahertz wave detection chip according to claim 5, wherein the hydrophilic layer comprises a plastic film with hydrophilic coating.

7. The terahertz wave detection chip according to claim 1, wherein the hydrophilic layer is disposed between the substrate and the metamaterial layer, and the hydrophilic layer is adhered to the surface of the substrate.

8. The terahertz wave detection chip according to claim 7, wherein the hydrophilic layer comprises a plastic film with hydrophilic coating or a glass cloth tape.

9. A terahertz wave detection chip, comprising:
   a substrate; and
   at least one detection structure disposed on a surface of the substrate, wherein the at least one detection structure comprises a metamaterial layer and a hydrophilic layer, and the hydrophilic layer is disposed on the metamaterial layer;
   wherein a number of the at least one detection structure is multiple, and the detection structures are periodically arranged.

10. The terahertz wave detection chip according to claim 9, further comprising a hydrophobic coating disposed on the surface of the substrate, and the hydrophobic coating is located between any two of the detection structures adjacent to each other.

11. The terahertz wave detection chip according to claim 9, further comprising a partition disposed on the surface of the substrate, and the partition is located between any two of the detection structures adjacent to each other.

12. The terahertz wave detection chip according to claim 9, wherein an area of each of the detection structures is equal to or less than $100.0 \text{ mm}^2$, and a distance between any two of the detection structures adjacent to each other is greater than 2.0 mm.

13. The terahertz wave detection chip according to claim 9, wherein the metamaterial layer has a plurality of regions, and each of the regions has a plurality of resonance elements.

14. The terahertz wave detection chip according to claim 13, wherein the resonance elements in each of the regions are periodically arranged to form a resonance pattern.

15. The terahertz wave detection chip according to claim 14, wherein the resonance patterns respectively correspond to a plurality of resonance frequencies, and the resonance frequencies are different from one another.

16. A terahertz wave detection system, comprising:
    a terahertz wave detection chip, comprising:
    a substrate; and
    a detection structure disposed on a surface of the substrate, wherein the detection structure comprises a metamaterial layer and a hydrophilic layer, the hydrophilic layer is disposed on the metamaterial layer, and the metamaterial layer comprises a resonance pattern;
    a transmitter configured to deliver a terahertz wave corresponding to the resonance pattern in the terahertz wave detection chip;
    a receiver configured to receive a reflected wave corresponding to the terahertz wave from the terahertz wave detection chip; and
    a processor in signal-transmittable connection with the receiver, wherein the processor obtains the reflected wave from the receiver and determines a detected object characteristic according to the reflected wave.

17. The terahertz wave detection system according to claim 16, wherein the processor is further in signal-transmittable connection with the transmitter, and the processor determines the detected object characteristic according to differences of physical properties between the terahertz wave and the reflected wave.

18. The terahertz wave detection system according to claim 17, wherein differences of physical properties comprise a frequency difference or an amplitude difference.

19. The terahertz wave detection system according to claim 16, further comprising a drying tool disposed corresponding to the terahertz wave detection chip.

20. The terahertz wave detection system according to claim 19, wherein the drying tool comprises a heater or a purge gas supplier.

* * * * *